(12) United States Patent
Pekonen

(10) Patent No.: US 8,554,312 B2
(45) Date of Patent: Oct. 8, 2013

(54) INTERFERENCE MITIGATION IN BIOMETRIC MEASUREMENTS

(75) Inventor: Elias Pekonen, Oulu (FI)

(73) Assignee: Polar Electro Oy, Kempele (FI)

( * ) Notice: Subject to any disclaimer, the term of this patent is extended or adjusted under 35 U.S.C. 154(b) by 0 days.

(21) Appl. No.: 13/323,964

(22) Filed: Dec. 13, 2011

(65) Prior Publication Data
US 2012/0157868 A1 Jun. 21, 2012

(30) Foreign Application Priority Data
Dec. 17, 2010 (FI) .................................... 20106338

(51) Int. Cl.
*A61B 5/0402* (2006.01)
*A61B 5/04* (2006.01)

(52) U.S. Cl.
USPC .......................... 600/509; 600/300; 324/71.1

(58) Field of Classification Search
USPC .................... 600/508, 509, 519, 520
See application file for complete search history.

(56) References Cited

U.S. PATENT DOCUMENTS

| | | | |
|---|---|---|---|
| 3,568,662 A | | 3/1971 | Everett et al. |
| 4,466,440 A | * | 8/1984 | Money et al. ............. 607/9 |
| 4,715,384 A | * | 12/1987 | Tabata ..................... 600/519 |
| 4,979,510 A | * | 12/1990 | Franz et al. ............. 600/374 |
| 5,582,181 A | * | 12/1996 | Ruess ....................... 600/508 |
| 6,496,721 B1 | | 12/2002 | Yonce |
| 2003/0006782 A1 | | 1/2003 | Shambroom et al. |
| 2006/0009691 A1 | | 1/2006 | Yeo et al. |
| 2007/0270918 A1 | * | 11/2007 | De Bel et al. ............. 607/48 |
| 2010/0219847 A1 | * | 9/2010 | Douglas ................. 324/686 |

FOREIGN PATENT DOCUMENTS

| | | |
|---|---|---|
| EP | 0085577 B1 | 6/1987 |
| EP | 0700658 A1 | 3/1996 |
| EP | 2042099 A1 | 4/2009 |
| WO | WO 2008135952 A1 * | 11/2008 |
| WO | WO2008135952 A1 | 11/2008 |

OTHER PUBLICATIONS

Jerry C. Whitaker ed., "The Electronics Handbook", CRC Press, 1996, p. 724.*
Tuomo Reiniaho, Finnish Search Report for corresponding Finnish Application No. 20106338, p. 1, Sep. 29, 2011.
Gunilla Kuster, European Search Report for corresponding European Application No. EP11193497, p. 1-2, Mar. 27, 2012.

* cited by examiner

*Primary Examiner* — Carl H Layno
*Assistant Examiner* — Erin Piateski
(74) *Attorney, Agent, or Firm* — Hoffmann & Baron, LLP

(57) ABSTRACT

A disclosed apparatus includes a first signal line configured to couple signals from a first electrode to a signal detection circuitry for measurement of biometric signals sensed by the first electrode; a second signal line configured to couple signals from a second electrode, which is different from the first electrode, to the signal detection circuitry for measurement of biometric signals sensed by the second electrode; and a coupling circuitry configured to selectively couple the first signal line and the second signal line to a common electrical potential so as to equalize electrical potential difference between the first electrode and the second electrode.

17 Claims, 5 Drawing Sheets

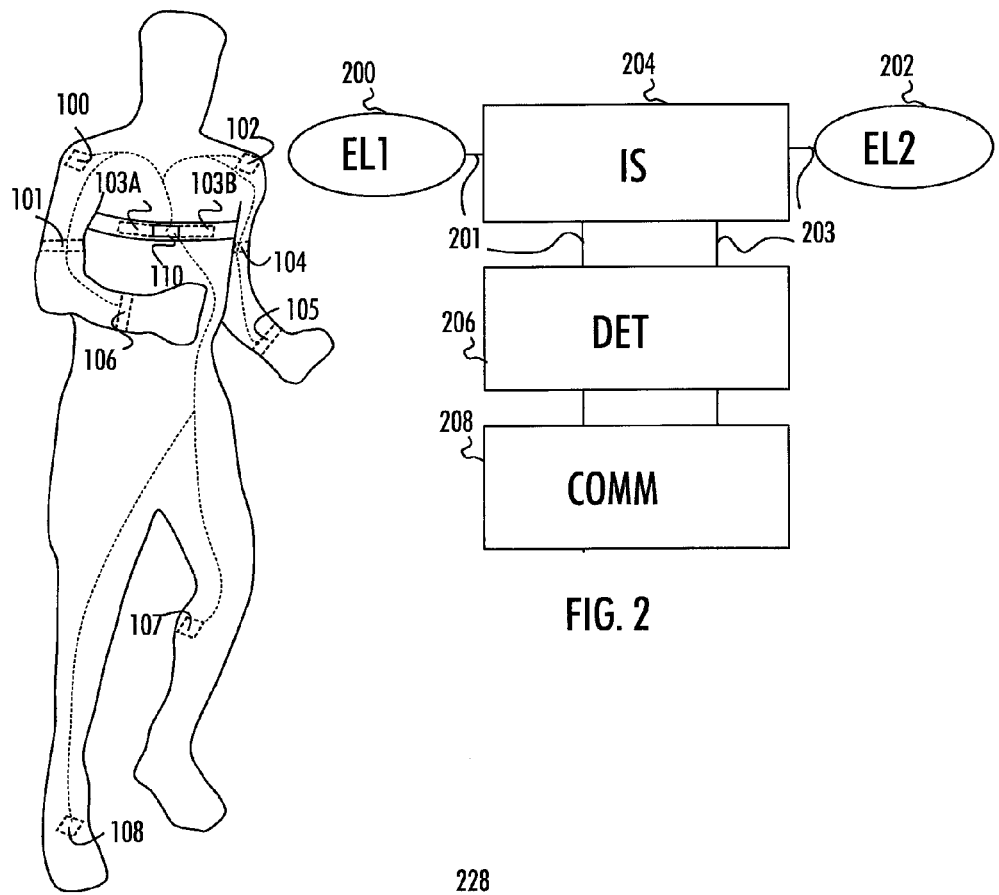
FIG. 1
FIG. 2
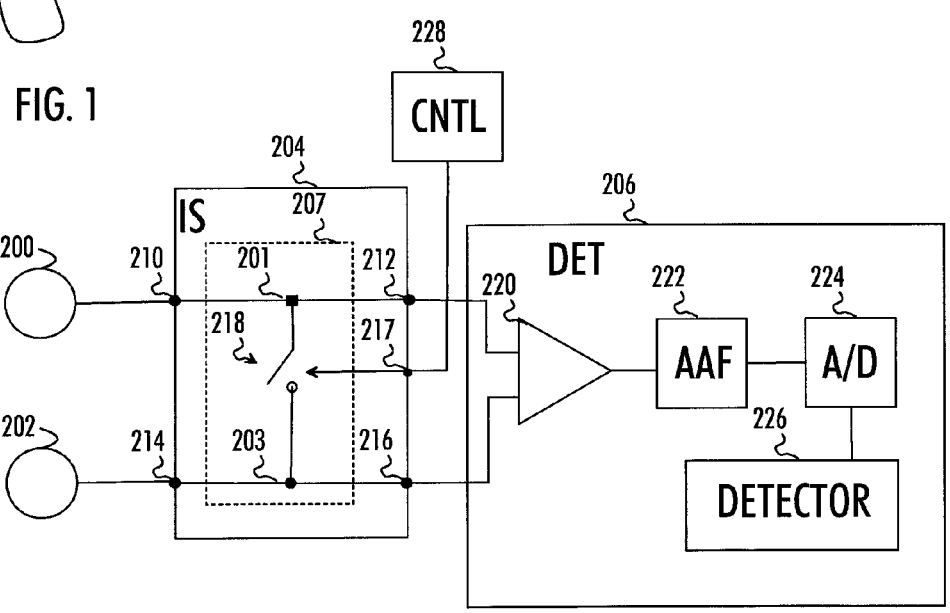
FIG. 3

INTERFERENCE MITIGATION IN BIOMETRIC MEASUREMENTS

CROSS-REFERENCE TO RELATED APPLICATION

This application claims priority based on Finnish Application No. 20106338, filed Dec. 17, 2010, which is incorporated herein by reference in its entirety.

BACKGROUND

1. Field

The invention relates to the field of measuring biometric signals.

2. Description of the Related Art

When measuring biometric signals, electrodes are in contact with a body of a subject whose biometric signals are being measured. Human skin contains electric charges that are typically distributed non-uniformly between measurement electrodes. Additionally, the contact between the electrodes and the subject's skin causes a triboelectric effect (also known as triboelectric charging). The triboelectric effect is a type of contact electrification in which materials in contact with each other become electrically charged as a result of their movement with respect to each other (such as through rubbing). The polarity and strength of the charges produced differ according to the materials, surface roughness, temperature, strain, and other properties. Therefore, the triboelectric effect is different for different electrodes in contact with the subject. As a result of these (and possible other) phenomena, electrical charges around one electrode are typically different from electrical charges around another electrode, which causes interference to the measurement of biometric signals.

SUMMARY

According to an aspect of the present invention, there is provided an apparatus comprising: a first signal line configured to couple signals from a first electrode to a signal detection circuitry for measurement of biometric signals sensed by the first electrode; a second signal line configured to couple a reference signal to a second input of the signal detection circuitry; and a coupling circuitry configured to selectively couple the first signal line and the second signal line to a common electrical potential, and to thereby cause a change in an electric potential of the first electrode and reduction in electrical potential difference between the first signal line and the second signal line.

According to another aspect, there is provided an apparatus comprising: a first signal line configured to couple signals from a first electrode to a signal detection circuitry for measurement of biometric signals sensed by the first electrode; a second signal line configured to couple signals from a second electrode, different from the first electrode, to the signal detection circuitry for measurement of biometric signals sensed by the second electrode; and coupling means for selectively coupling the first signal line and the second signal line to a common electrical potential so as to equalize electrical potential difference between the first electrode and the second electrode.

Embodiments of the invention are defined in the dependent claims.

BRIEF DESCRIPTION OF THE DRAWINGS

Embodiments of the present invention are described below, by way of example only, with reference to the accompanying drawings, in which FIG. 1 illustrates embodiments of measurement apparatuses for measuring biometric signals from a human body;

FIG. 2 illustrates a block diagram of a measurement apparatus according to an embodiment of the invention;

FIG. 3 illustrates a circuit diagram of an interference suppression circuitry comprised in a measurement apparatus according to an embodiment of the invention;

DETAILED DESCRIPTION

Figure 4A:
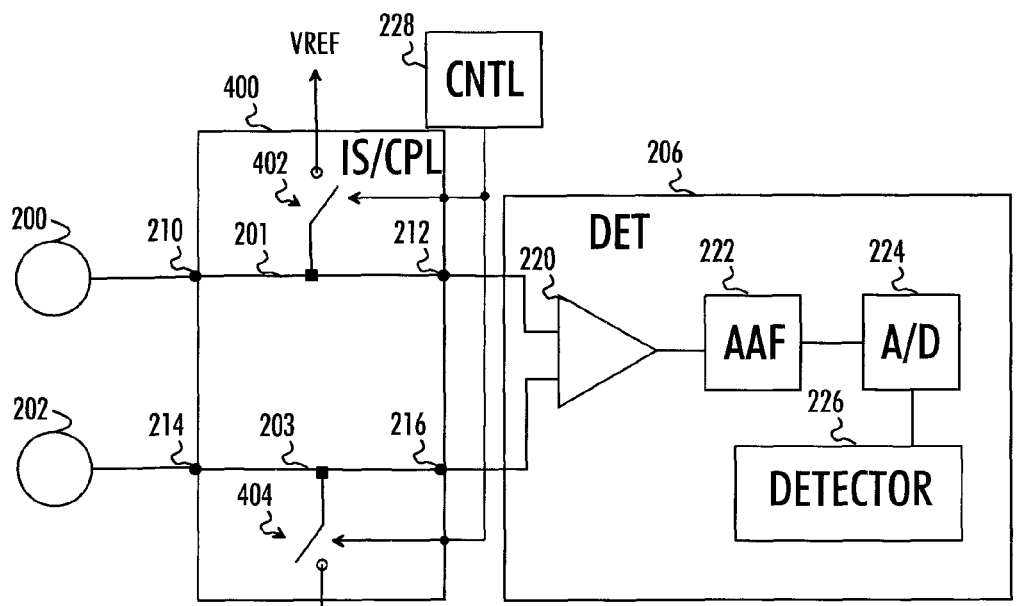
FIGS. 4A to 4C illustrate circuit diagrams of an interference suppression circuitries comprised in a measurement apparatus according to some embodiments of the invention.

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Embodiments described herein relate to a measurement apparatus or a measurement system configured to measure of biometric signals.

In an embodiment, the measurement apparatus is configured to measure a heart activity of a subject. The heart activity comprises electrocardiograph (EKG) or a part thereof, heart rate, heart beat intervals, heart beat timing and heart rate variability.

In an embodiment, measurement apparatus is configured to measure muscle activity with a electromyography (EMG).

The subject may be a human body or an animal. Referring to FIG. 1, the measurement apparatus or the measurement system may comprise a plurality of electrodes 100 to 108 configured to be placed into physical contact with the skin of the human body in order to carry out the measurement of the biosignal. The electrodes 100 to 108 may be attached to various locations in the human body, e.g. chest, shoulder(s), arm(s), wrist(s), and leg(s), as illustrated in FIG. 1. In an embodiment, the measurement device is a heart rate transmitter 110 comprising a measurement circuitry and a strap designed to be attached around the chest of the human or an animal. The measurement circuitry comprises the electrodes 103A and 103B that are in contact with the skin in the chest area.

A skin electrode 100 to 108 may be coupled to the measurement circuitry, which is exemplified with the heart rate transmitter 110 in FIG. 1. The measurement circuitry receives the biosignals from the skin electrode 100 to 108, as illustrated by dashed lines connecting the electrodes 100 to 108 and the heart rate transmitter 110, and subjects the biosignals to signal processing.

In an embodiment of the invention, at least one skin electrode 100 to 108 is integrated into an apparel, such as a shirt. The apparel may comprise conducting means, such as wires or flex structures, which enable transferring the biosignals from the skin electrode 100 to 108 to the measurement circuitry 110. The measurement circuitry itself may be located in an arbitrary location in the apparel, and it may be fixed to the apparel.

FIG. 2 illustrates a general block diagram of the measurement apparatus according to an embodiment of the invention. The measurement apparatus comprises a first electrode 200 and a second electrode 202 that are designed to sense bodily currents in the body of the subject and forward them as electrical signals in the measurement apparatus. The measurement apparatus further comprises an interference suppression circuitry 204 configured to suppress the interference caused by different electrical charges in the electrodes 200, 202. The interference suppression circuitry 204 is an apparatus that comprises a first signal line 201 configured to couple signals from the first electrode 200 to a signal detection circuitry 206 for measurement of biometric signals sensed by the first electrode 200. The measurement apparatus further comprises a second signal line 203 configured to couple signals from the second electrode 202 to the signal detection circuitry 206 for measurement of biometric signals sensed by the second electrode 202. The apparatus further comprises a coupling circuitry configured to selectively couple the first signal line 201 and the second signal 203 line to a common electrical potential, and to thereby cause a change in the electric potential of at least one of the electrodes 200, 202 so as to equalize or at least reduce electrical potential difference between the first electrode 200 and the second electrode 202. The potential difference is reduced, as the connection of the electrodes 200, 202 to the common electrical potential causes movement of charges between the electrodes 200, 202 and the common potential. The selective coupling enables the suppression of interference caused by the different charges in the electrodes 200, 202 in a controlled manner, which result in a more accurate measurement of the biometric signals while not interfering with the measurement process.

In an embodiment of the invention, the selective coupling and the control thereof incorporate a controlled time structure when coupling the first signal line 201 and the second signal line 203 to the common electric potential. In an embodiment, the time structure comprises time instants when the first signal line 201 and the second signal line 203 are coupled simultaneously to the common electric potential. In another embodiment of the invention, the time structure comprises time instants when the first signal line 201 and the second signal 203 line are coupled to the common electric potential at different time instants.

The signal detection circuitry 206 is configured to detect signals sensed by the first and the second electrodes 200, 202. In an embodiment, the signal detection circuitry 206 is configured to detect a determined waveform in the biometric signal(s) received from the electrodes 200, 202. The detected waveform may then be used to compute various parameters from the biometric signal, e.g. the heart activity. The measurement apparatus may further comprise a communication circuitry 208 configured to transmit the measured biometric signals and/or any other biometric information obtained from the measurement to an external receiver apparatus. The communication circuitry 208 may comprise a wireless communication circuitry and/or a wired communication circuitry, and the biometric information may be transmitted through the communication circuitry in order to display the biometric information through a user interface.

FIG. 3 illustrates an embodiment of the interference suppression circuitry 204. The interference suppression circuitry 204 comprises a first input terminal 210 connected to the first electrode 200, and a second input terminal 214 connected to the second electrode 202. The interference suppression circuitry 204 further comprises a first output terminal 212 connected to the first input terminal 210, and a second output terminal 216 connected to the second input terminal 214. The output terminals 212 and 216 are further connected to respective input terminals of an input interface of the signal detection circuitry 206.

The interference suppression circuitry 204 further comprises the coupling circuitry 207 according to an embodiment of the invention. In some embodiments, the coupling circuitry 207 forms the interference suppression circuitry, while in other embodiments the interference suppression circuitry comprises additional components. The coupling circuitry 207 is in this embodiment arranged to comprise a switch 218 that is responsive to a control signal external to the interference suppression circuitry 204, wherein the control signal selectively closes and opens the switch 218. The interference suppression circuitry 204 may further comprise a third input terminal 217 for receiving the control signal from a controller 228 that is conveyed to the switch 218. A first terminal of the switch 218 may be connected to the first signal line 201 comprising the first input terminal 210 and the first output terminal 212, and a second terminal of the switch 218 may be connected to the second signal line 203 comprising the second input terminal 214 and the second output terminal 216. The signal lines needed to connect the switch 218 to the signal lines 201, 203 may be comprised in the coupling circuitry. In operation, the switch 218 selectively couples, e.g. short circuits, the first signal line 201 to the second signal line 203 in response to the control signal. As a consequence, the potential difference between the first and the second electrode 200, 202 is equalized, and the equalization is carried out before the signal detection circuitry 206.

In an embodiment, the input terminals 210, 214 and the output terminals 212, 216 may be logical terminals or both logical and physical terminals. For example, when the electrodes 200, 202 are detachable from the interference suppression circuitry 204, connectors connecting and disconnecting the electrodes 200, 202 to/from the interference suppression circuitry 204 may be provided in which case such connectors may be construed to form the input terminals 210, 214.

In an embodiment, the electrodes 200, 202 are integrated into the interference suppression circuitry 204, and a single continuous signal line with no connectors may be provided from the electrodes 200, 202 to the outputs of the interference suppression circuitry 204. Similarly for the output terminals 212, 216, if the signal detection circuitry 206 is detachable from the interference suppression circuitry 204, connectors connecting and disconnecting the electrodes 200, 202 to/from the interference suppression circuitry 204 may be provided in which case such connectors may be construed to form the output terminals 212, 216.

In an embodiment, the interference suppression circuitry 204 is integrated with the signal detection circuitry 206, and a single continuous signal line with no connectors may be provided from the respective input terminals to the input of the signal detection circuitry 206. As a consequence, a single signal line may be provided from each electrode to the input of the signal detection circuitry 206, and no physical terminals may be provided in the interference suppression circuitry, except optionally for the control signal controlling the switch 218.

The signal detection circuitry 206 may comprise an amplifier 220 configured to amplify the signal received through the first and second signal lines 201, 203 from the respective electrodes 200, 202. The amplifier 220 may be a differential amplifier, and an impedance circuit may be provided at the input of the amplifier so as to tune an input impedance of the signal detection 206 circuitry and the differential amplifier. The signal detection circuitry 206 may further comprise an anti-aliasing filter 222 connected to an output of the amplifier 220 and configured to remove high frequency components that might cause aliasing in an analog-to-digital conversion. The anti-aliasing filter 222 may output a filtered and amplified signal to an analog-to-digital (A/D) converter 224 configured to sample the received (analog) signal and convert it into a digital signal. The digital signal may then be applied to a detector 226 that is arranged to detect determined events in the received signal, e.g. determined waveforms, peaks, etc.

In an embodiment, the detector 226 may be configured to operate in an analog domain and, accordingly, an input of the detector 226 may be connected to an output of the amplifier 220, and the anti-alias filtering and the ND conversion may follow the detector 226, or they may even be omitted. Such a detector 226 operating in the analog domain may comprise a peak detector, for example.

It should be noted that while the embodiments described herein relate to a measurement apparatus comprising two electrodes 200, 202, the measurement apparatus may comprise a single electrode 200, and a reference signal may be provided to another input of the differential amplifier 220 by connecting the other input to a reference voltage source or to the ground, for example. In the embodiments described herein, one of the electrodes 200, 202 may be understood as a reference electrode providing the differential amplifier with the reference signal, e.g. a reference voltage, while the other electrode 200, 202 provides the measurement signal.

As described above, some embodiments of the invention provide the coupling circuitry 207 in the interference suppression circuitry 204 in order to equalize the electrical potential difference between the electrodes 200, 202. While FIG. 3 illustrates an embodiment of the interference suppression circuitry 204 that provides a simple, yet effective circuit configuration by short-circuiting the signal lines 201, 203, the signal lines 201, 203 may each be connected to a common, third potential.

Figure 4B:
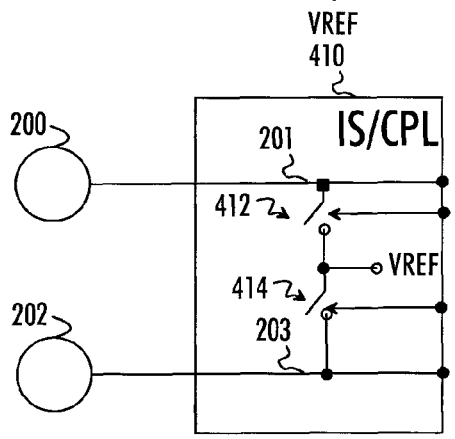
Figure 4C:
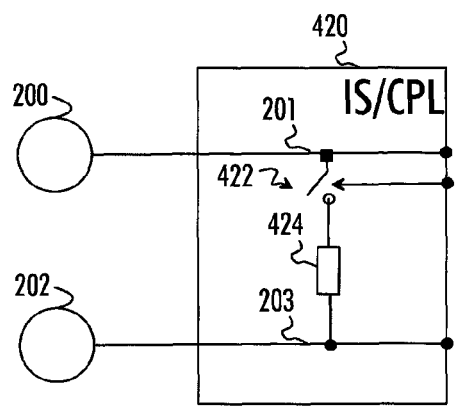
Figure 5:
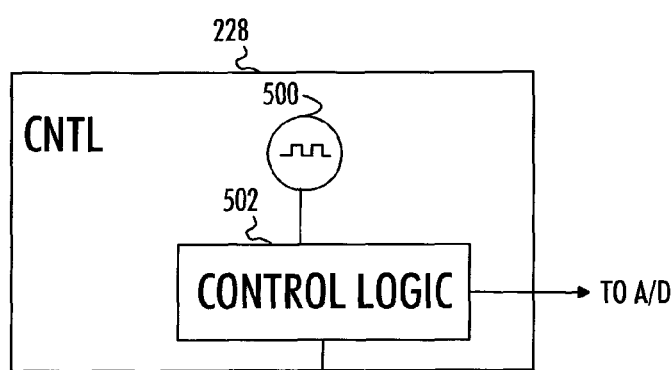
FIG. 5 illustrates a circuit diagram of a controller comprised in FIGS. 3 and 4.

FIGS. 4A, 4B, and 4C illustrate further embodiments of the interference suppression circuitry 204. In these embodiments, the interference suppression circuitry consist of the coupling circuitry 400, 410, 420. However, the interference suppression circuitry may in other embodiments comprise additional components, as mentioned above. FIG. 4A illustrates a circuit diagram of an embodiment, where both signal lines 201, 203 are connected separately to a common reference potential Vref that is not the potential of either electrode 200, 202. The reference potential Vref may be a potential or a voltage that is kept constant in the measurement apparatus comprising the interference suppression circuitry according to this embodiment. The reference potential may be the ground, or it may be a non-zero potential.

Referring to FIG. 4A, the coupling circuitry 400 according to this embodiment comprises a first switch 402 having its one terminal connected to the first signal line 201 (connecting the first electrode 200 to the signal detection circuitry 206) and the other terminal connected to the reference potential Vref. The coupling circuitry further comprises a second switch 404 having its one terminal connected to the second signal line 203 (connecting the second electrode 202 to the signal detection circuitry 206) and the other terminal connected to the reference potential Vref. The switches 402, 404 may be opened and closed simultaneously or at different times by applying a control signal to the switches 402, 404 from the controller 228. As a consequence, the switches 402, 404 comprised in the coupling circuitry equalize, in response to the control signal, the potential difference between the electrodes 200, 202. In FIG. 4A, the components denoted by the same reference numerals as in FIGS. 2 and 3 may have the same structure and/or functionality, and the description of them is omitted for the sake of conciseness.

FIG. 4B illustrates an embodiment of the coupling circuitry 410 that combines the embodiments of FIGS. 3 and 4A. Referring to FIG. 4B, the coupling circuitry 410 is formed between the first and second signal line 201, 203 to selectively couple the signal lines 201, 203 to each other and to a common reference potential Vref that is applied between the signal lines 201, 203. The coupling circuitry 410 comprises in this embodiment two switches: a first switch 412 coupled to the first signal line 201 and a second switch 414 coupled between the first switch 412 and the second signal line 203. The reference potential Vref is applied to a signal line between the switches 412, 414. The switches 412, 414 are selectively closed and opened according to the control signals provided by the controller 228. The controller 228 may be configured to apply the same control signal to both switches 412, 414, thereby closing and opening the switches 412 simultaneously and thus implementing the selective coupling of the signal lines 201, 203. The control signal may be a clock signal, and the clock signal with same properties (frequency and phase) may be applied to all switches 412, 414 of the coupling circuitry 410. The reference potential Vref may be a biasing voltage of the differential amplifier 220 in both embodiments of FIGS. 4A and 4B. Therefore, the reference potential Vref may be selected to provide a potential that is between operational voltages of the differential amplifier 220, thereby tuning the signal level according to a dynamic range of the differential amplifier 220.

FIG. 4C illustrates yet another embodiment, wherein the coupling circuitry 420 comprises further components. It should be appreciated that one or more other components may be included in the coupling circuitry, e.g. any one of the coupling circuitries of the embodiments of FIGS. 3, 4A, and 4B. Referring to FIG. 4C, this embodiment of the coupling circuitry 420 comprises at least one switch 422 carrying out the coupling of the signal lines 201, 203 to each other (or to a common potential). The coupling circuitry 420 further comprises, for example, a resistor 424 in series with the switch 422. The resistor may also represent internal resistance of the switch(es) comprised in the coupling circuitry 420. The resistor 424 may also include inherent reactive properties in the form of parasitic capacitance and inductance. Embodiments where additional components are included in the coupling circuitry 420 also reduce the potential difference between the electrodes 200, 202, although the embodiments may require a longer duration to equalize the potential difference between the electrodes 200, 202, depending on the properties of the components.

In the above-described embodiments, and generally in other embodiments, the number of electrodes is not limited to two, and the number of electrodes may be higher than two, e.g. three, four, etc. With respect to the embodiment of FIG. 3, the interference suppression circuitry 204 may be configured to couple the electrodes by short-circuiting them according to the control signal controlling the short-circuiting. One of the electrodes may be selected as a reference electrode, and the other electrodes may be connected to the reference electrode so as to equalize the potential difference, e.g. by adjusting the potential of the other electrodes to match with the potential of the reference electrode. Referring to FIGS. 4A, 4B and 4C, the reference potential Vref may be the potential of the reference electrode or it may be the fixed potential, as described above.

Let us now consider the control signal(s) and the controller 228 controlling the operation of the switches 218, 402, 404. The controller 228 may comprise a clock signal generator 500 configured to generate a clock signal. The clock signal generator 500 may be a square wave oscillator, for example. The clock signal generated by the clock signal generator 500 may be output to a control logic circuitry 502 configured to modify the clock signal to produce the control signal(s) applied to the switches 218, 402, 404. The control logic circuitry 502 may be configured to modify the input clock signal into a plurality of clock signal(s) and, optionally, adjust properties of the clock signals. The control logic circuitry 502 may be configured to modify at least one of the phase and duty cycle of the clock signals to produce the control signal(s).

In an embodiment, the control logic circuitry 502 is configured to output a plurality of output clock signals, wherein at least one of the output clock signals is applied to the switch(es) 218, 402, 404 (depending on the circuit and number of switches in the interference suppression circuitry 204, 400, 410, 420), and at least one of the output clock signals is applied to another component of the apparatus, e.g. the A/D converter 224. The control logic circuitry 502 may be configured to modify the clock signals such that the clock signals applied to the switches, e.g. switches 402, 404, are identical. This controls the plurality of switches to open and close simultaneously. In another embodiment, the control logic circuitry 502 is be configured to modify the clock signals such that the clock signals applied to the switches, e.g. switches 402, 404, are not identical. Accordingly, the different switches 402, 404 may be connected to the reference potential Vref alternately. In an embodiment, the control logic circuitry 500 is configured to modify the clock signals applied to the switch(es) such that they differ from clock the signal(s) applied to the other component(s) in at least one of the phase and the duty cycle. This may be used to control that the switch(es) 218, 402, 404 are not closed at a sampling instant of the ND converter 224. This is discussed in greater detail with reference to timing diagrams of FIGS. 7 to 9.

Figure 6:
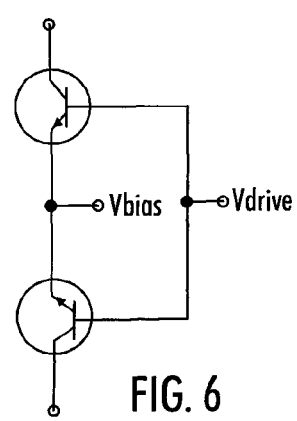
FIG. 6 illustrates an embodiment of a circuit diagram for a switch used in the interference suppression circuitry according to an embodiment of the invention.

FIG. 6 illustrates an embodiment of a switch which may constitute any one of the switches 218, 402, 404. In this embodiment, the switch is formed by two bipolar transistors arranged as illustrated in FIG. 6. A signal Vdrive applied to bases of the two transistors is the above-mentioned clock signal, and Vbias refers to a bias voltage. Terminals of the switches may be connected to at least one of the signal lines of the interference suppression circuitry, as described above in connection with FIGS. 3 and 4. It should be appreciated that instead of the bipolar transistors, field effect transistors may be used to realize the switches 218, 402, 404.

Figure 7:
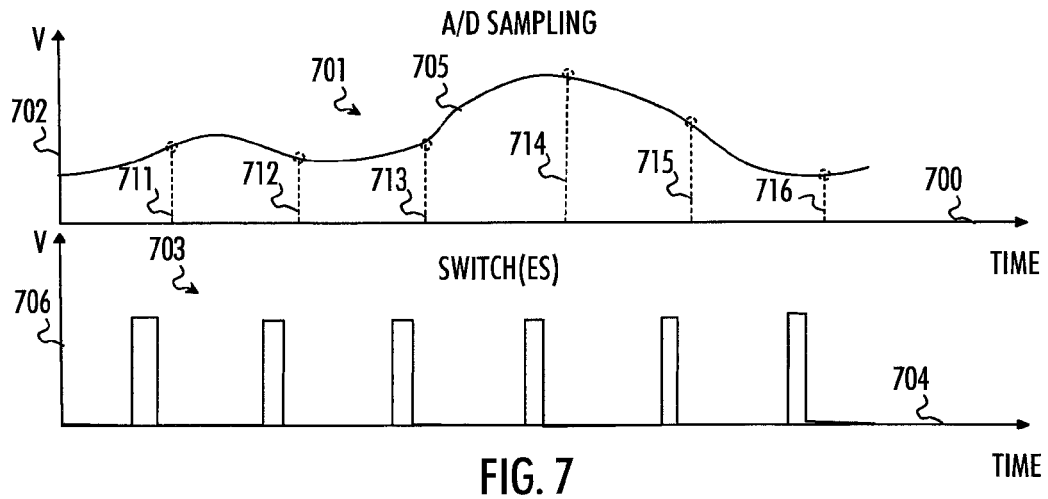
FIGS. 7 to 9 illustrate embodiments for timing the operation of the interference suppression circuitry according to some embodiments of the invention.
Figure 8:
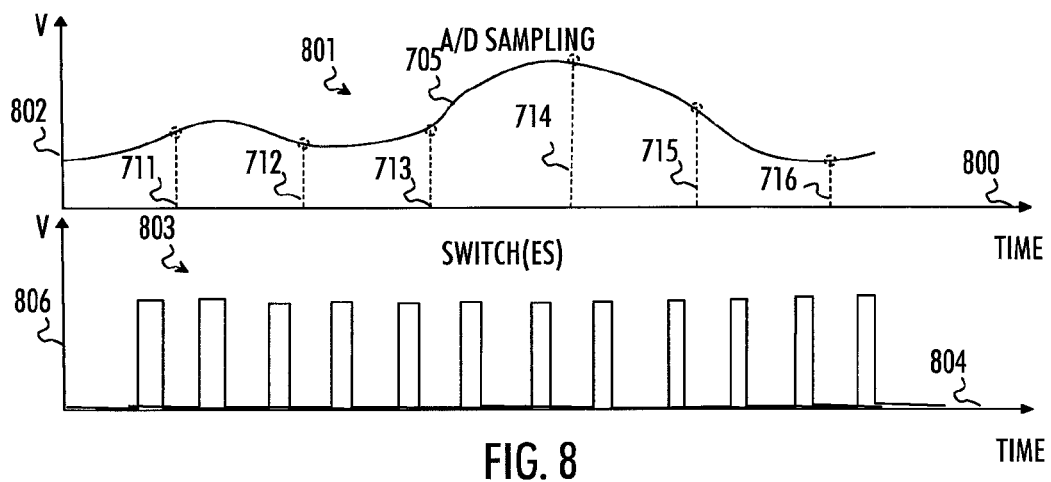
Figure 9:
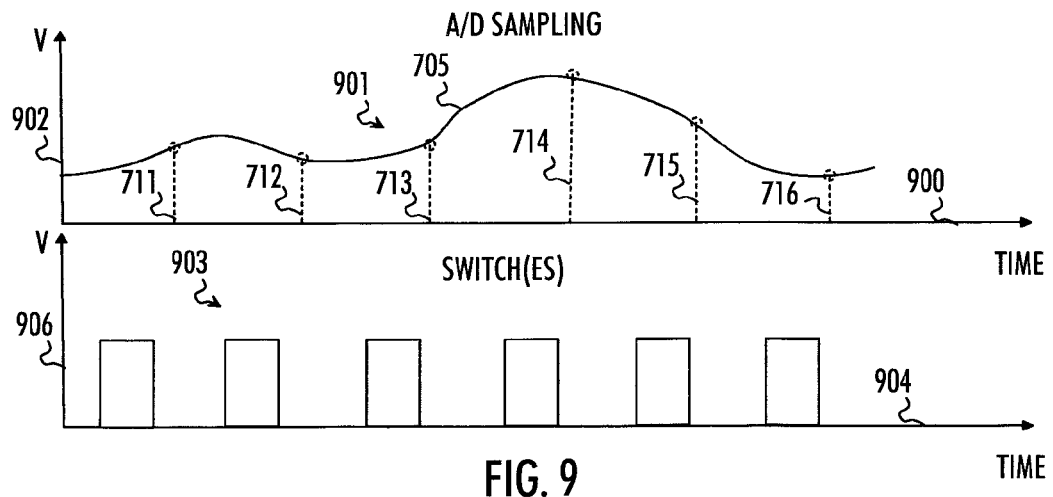

Let us now consider embodiments for controlling the operation of the switches with respect to a sampling instant of the ND converter 224 configured to A/D convert the signal received from the electrodes. FIGS. 7 to 9 illustrate such embodiments. In each FIGS. 7 to 9, two graphs are illustrated. A horizontal axis 700, 704, 800, 804, 900, 904 denotes time, and a vertical axis 702, 706, 802, 806, 902, 906 denotes voltage or amplitude. A topmost graph 701, 801, 901 in each Figure illustrates as a solid, continuous line 705 an analog signal received by the ND converter 224 and sampling instants of the ND converter 224 as vertical dashed lines with dots 711 to 716 marking samples acquired by the ND converter 224. Let us note that the signal illustrated in FIGS. 7 to 9 is an arbitrary signal and, in practice, the signal may be the biometric signal (e.g. a heart activity signal) sensed by the electrodes 200, 202. The lower graph 703, 803, 903 in each FIGS. 7 to 9 illustrates time intervals when the switches 218, 402, 404 of the interference suppression circuitry 204 are open and closed. The signal illustrated in the lower graphs 703, 803, 903 is the clock signal controlling the switches 218, 204, 404. When the clock signal is HIGH (has a higher voltage/amplitude), the switches 218, 402, 404 are closed and conduct current, and when the clock signal is LOW (has a lower voltage/amplitude), the switches 218, 402, 404 are open and do not conduct current. It should be understood that the switches 218, 402, 404 may also be configured to open when the clock signal is HIGH and to close when the clock signal is LOW, depending on the implementation of the switches 218, 402, 404.

Referring to FIG. 7, the switches 218, 402, 404 are closed and the potential difference between the electrodes 200, 202 is equalized between sampling instants of the A/D converter 224. As a consequence, the interference caused by the potential difference is suppressed between the sampling instants, and the interference does not propagate to the A/D conversion. In this embodiment, the frequency of the clock signal closing the switches 218, 402, 404 is the same as the frequency of the sampling instants of the ND converter 224. However, in other embodiments where the interference is lower, the frequency of the sampling instants of the ND converter 224 is a multiple (higher than one) of the frequency of the clock signal closing the switches 218, 402, 404. In such a case, the interference suppression is carried out less frequently, and there may be a plurality of consecutive sampling instants with no interference suppression interval between them. On the other hand, the frequency of the clock signal may be a multiple (higher than one) of the frequency of the sampling instants of the A/D converter 224 and, thus, a plurality of interference suppression intervals may be provided between the sampling instants, as illustrated in FIG. 8. FIG. 9 illustrates an embodiment where the duty cycle of the clock signal controlling the switches is higher than in FIGS. 7 and 8. In other words, the clock signal is HIGH for a longer time interval than in the embodiments of FIGS. 7 and 8 and, as a consequence, the switches 218, 402, 404 are closed for a longer duration. In an embodiment, the duration when the switches 218, 402, 404 are closed at a time is longer than the duration when the switches 218, 402, 404 are open so that the interference suppression interval is longer than a time interval between consecutive interference suppression intervals. The sampling instant may still be configured to be provided between the interference suppression intervals.

In all embodiments of FIGS. 7 to 9, an interference suppression interval is provided just before the sampling instant. Therefore, according to some embodiments, the interference suppression circuitry 204 is configured to couple the electrodes 200, 202 to the common potential during a latter half of a time interval between consecutive sampling instants of the analog-to-digital converter. Such embodiments reduce the amount of potential difference that may be generated in the electrodes 200, 202 before a given sampling instant.

The switches 218, 402, 404 driven by the clock signal also operate as a frequency mixer, thereby resulting in a signal that has intermodulation distortion. In order to separate frequency components caused by the intermodulation, the frequency of the clock signal may be selected to be higher than a highest frequency component of the measured biometric signal. For example, the highest frequency component of a heart activity signal is less than 100 Hz and, thus, the frequency of the clock signal may be higher than 100 Hz, e.g. between 100 and 500 Hz. As a consequence, a filter located between the interference circuitry and the detector, e.g. the anti-aliasing filter 222, may be configured to have a pass-band that excises intermodulation components to avoid aliasing in the ND conversion and/or interference in the detection.

In an embodiment, the frequency of the clock signal functioning as the control signal is more than 500 Hz.

In an embodiment, the frequency of the clock signal functioning as the control signal is between 10 and 100 Hz.

Figure 10:
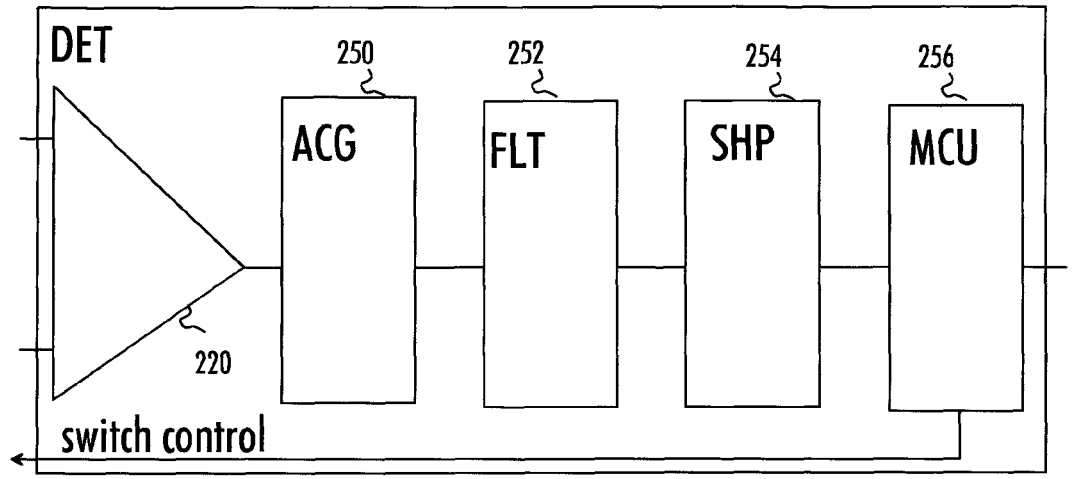
FIGS. 10 and 11 illustrate embodiments of a signal detection circuitry according to an embodiment of the invention.
Figure 11:
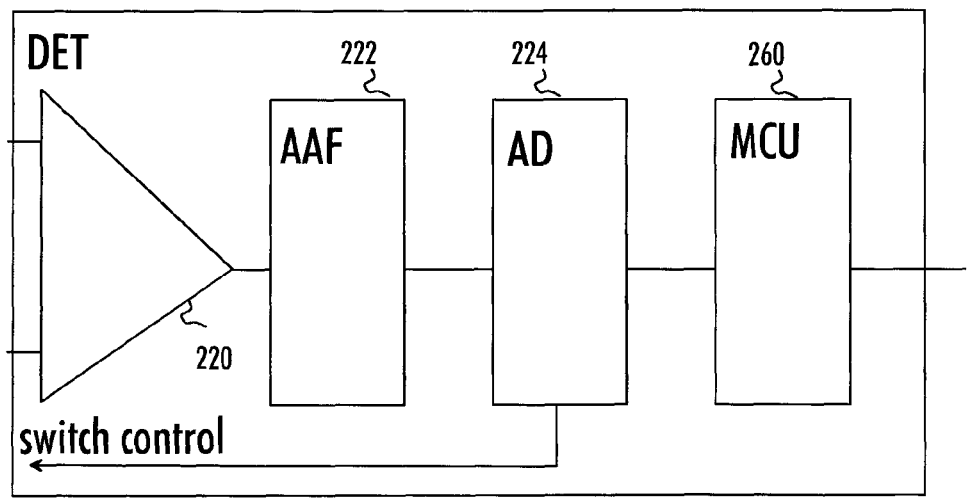

FIGS. 10 and 11 illustrate embodiments of the signal detection circuitry 206. FIG. 10 illustrates an embodiment of an analog signal detection circuitry. The analog signal detection circuitry may comprise the differential amplifier 220, another amplifier 250 connected to an output of the differential amplifier 220 and configured to adjust a gain of a signal received from the differential amplifier 220. The amplifier 250 may be an automatically controlled gain (ACG) amplifier. The amplifier 250 may apply its output signal to a filter 252 arranged to filter undesired signal components and apply the filtered signal to a waveform shaper circuitry 254 configured to shape a waveform of the filtered signal in order to modify the signal to have a waveform that is suitable for the detection. The shaped signal may then be applied to a microcontroller unit 256 that may comprise a detector detecting a determined signal component in the shaped signal, e.g. a peak. In this embodiment, the microcontroller unit 256 may be configured to control the interference suppression circuitry to carry out the potential equalization. Accordingly, the microcontroller unit 256 may be configured to output the control signal that operates the switches 218, 402, 404. Outputting a control signal that operates the switches to carry out the equalization may be triggered by a determined event. For example, the microcontroller unit 256 may be configured to output the control signal upon detecting the determined signal component in the shaped signal. In other embodiments, the microcontroller unit 256 may further comprise a signal quality estimator that is configured to evaluate the received signal in order to determine the degree of interference in the received signal. The signal quality estimator may calculate a signal-to-noise ratio (SNR) estimate of the received signal, for example, or another signal quality estimate. When the signal quality estimate indicates that the interference in the received signal exceeds a predetermined threshold, e.g. when the SNR drops below the threshold, the microcontroller unit 256 may be configured to carry out the potential equalization by closing the switches 218, 402, 404.

FIG. 11 illustrates an embodiment of a digital signal detection circuitry. The signal detection circuitry may comprise the differential amplifier 220, the anti-aliasing filter 222, and the A/D converter 224. The ND converted signal may be applied to a digital microcontroller unit 260 for the signal detection. In this embodiment, the control signal for operating the switches may be output from the ND converter 224 to enable the potential equalization at time instants when the A/D converter 224 is not sampling the signal, as described in embodiments of FIGS. 7 to 9. However, the control signal may be provided by the microcontroller unit 260 in a manner similar to the embodiments described above in connection with FIGS. 7 to 9, and in connection with the functionality of the microcontroller unit 256 of FIG. 10. The microcontroller unit 260 may be configured to carry out the control of the interference suppression circuitry 204, 400 in a computer process. In response to reading a computer program product embodied on a computer-readable memory apparatus, the microcontroller unit 260 executes the computer process carrying out the equalization of the potential difference between the electrodes according to any one of the above-described embodiments.

Figure 12:
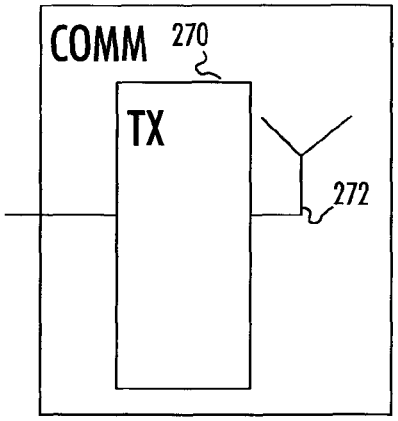
FIG. 12 illustrates an embodiment of a communication circuitry.

The signal detection circuitry 206 may be connected to the communication circuitry 208, as described above in connection with FIG. 2. FIG. 12 illustrates an embodiment of the communication circuitry 108, wherein the communication circuitry comprises a transmitter circuitry 270 and an antenna 272. The transmitter circuitry 270 may be provided with appropriate electronics to implement a transmitter according to a wireless communication specification used for conveying the measured biometric signal over an air interface. The transmitter circuitry 270 may also comprise receiver electronics, when the apparatus carrying out embodiments of the invention is configured to receive commands, data, or other signals from another communication apparatus. In an embodiment, the transmitter circuitry 270 is a Bluetooth-based transceiver, such as Bluetooth Low Energy (BLE). In an embodiment, the transmitter circuitry 270 is an ANT transceiver originally introduced by Dynastream Innovations. In an embodiment, the transmitter circuitry 270 is a Zigbee transceiver based on IEEE 802.15.4 standard or its derivative. In an embodiment, the transmitter circuitry 270 is a WiFi transceiver based on IEEE 802.11x standard. In an embodiment of the invention, the transmitter circuitry 270 comprises at least two transceivers selected from the group comprising: Bluetooth or its derivatives, ANT or its derivatives, Zigbee or its derivatives, WiFi or its derivatives. In an embodiment, the transmitter circuitry 270 comprises a transmitter based on inductive transmission.

As used in this application, the term 'circuitry' refers to all of the following: (a) hardware-only circuit implementations, such as implementations in only analog and/or digital circuitry, and (b) to combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

Figure 13:
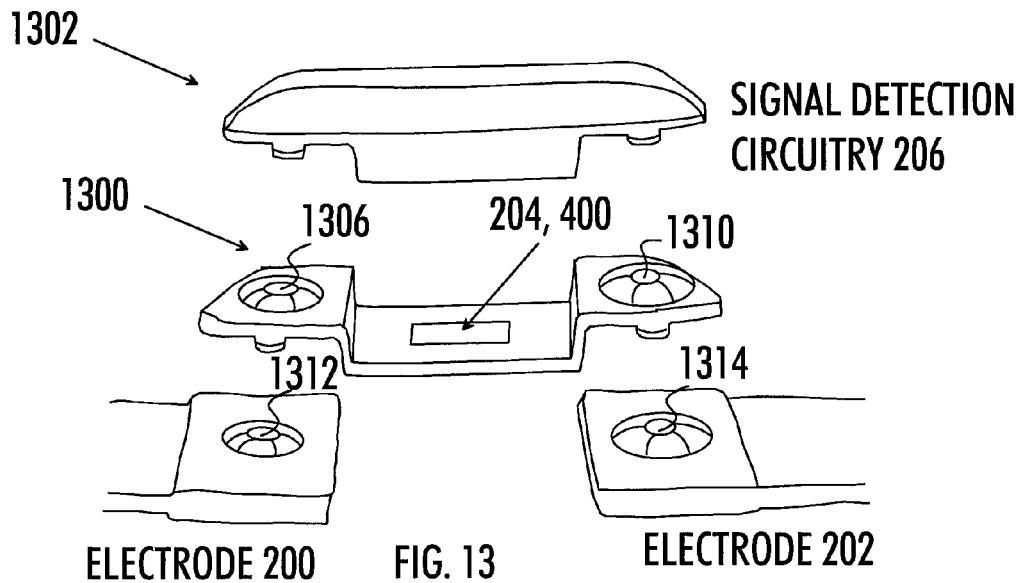
FIGS. 13 to 15 illustrate embodiments of apparatuses comprising the interference suppression circuitry according to some embodiments of the invention.
Figure 14:
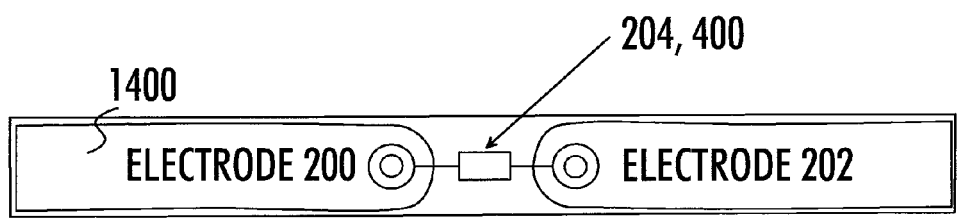
Figure 15:
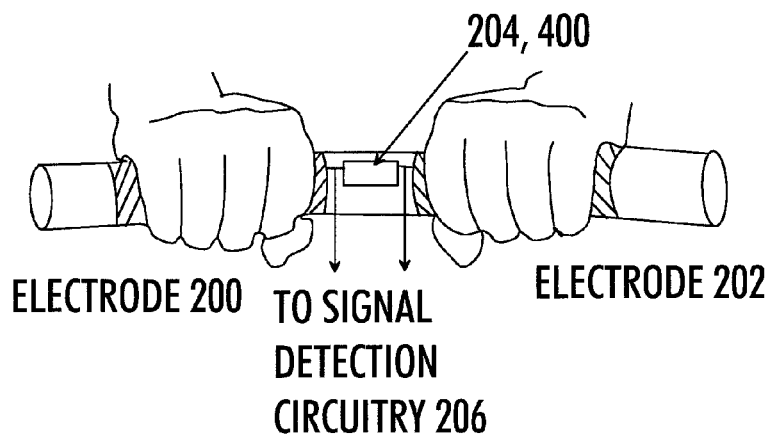

FIGS. 13 to 15 illustrate embodiments of apparatuses comprising the interference suppression circuitry according to some embodiments of the invention.

FIG. 13 illustrates an embodiment where the interference suppression circuitry 204, 400 is detachable from the electrodes 200, 202 and from the signal detection circuitry 206. The electrodes 200, 202 may comprise connectors 1312, 1314 to which a casing 1300 comprising the interference suppression circuitry 204, 400 may be attached. On the other hand, a casing 1302 of the signal detection circuitry 206 may then be connected to connectors 1306, 1310 of the casing 1300 of the interference suppression circuitry, as illustrated in FIG. 13 in order to achieve the circuit diagram of FIG. 3 or 4, for example. The casing 1300 and the interference suppression circuit 204, 400 together form a modular structure which may further comprise the controller 228 for generating the control signal for the interference suppression circuitry 204, 400, 410, 420.

FIG. 14 illustrates an embodiment where the measurement apparatus is a strap 1400 to be placed around the chest of the subject. The electrodes 200, 202 and the interference suppression circuitry 204, 400 may be integrated in the strap 1400. FIG. 15 illustrates a measurement apparatus configured to measure the biometric signals from hands of the subject and, thus, the electrodes 200, 202 may be arranged in a location from which the subject grips the measurement apparatus. The interference suppression circuitry 204, 400 may again be integrated to the measurement apparatus to selectively couple the electrodes to the common potential.

It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
a first signal line configured to couple signals from a first electrode to a signal detection circuitry for measurement of biometric signals sensed by the first electrode;
a second signal line configured to couple a reference signal to a second input of the signal detection circuitry; and
a coupling circuitry configured to selectively couple the first signal line and the second signal line to a common electrical potential, and to thereby cause a change in an electric potential of the first electrode and reduction in electrical potential difference between the first signal line and the second signal line, wherein the selective coupling of the coupling circuitry is synchronized with a clock signal controlling sampling instants of an analog-to-digital converter of the apparatus such that the selective coupling is performed between consecutive sampling instants of an analog-to-digital converter without performing selective coupling during sampling instants of the analog-to-digital converter.

2. The apparatus of claim 1, wherein the second signal line is connected to a ground or to a second electrode, different from the first electrode.

3. The apparatus of claim 1, wherein the coupling circuitry is configured to equalize the electrical potential difference between the first signal line and the second signal line.

4. The apparatus of claim 1, wherein the coupling circuitry comprises at least one switch coupling, when closed, the first signal line and the second signal line to the common electrical potential, and wherein the at least one switch is responsive to at least one external control signal.

5. The apparatus of claim 1, wherein the coupling circuit is configured to couple the first signal line and the second signal line to a common electrical potential by creating a short circuit between a first input terminal and a second input terminal.

6. The apparatus of claim 1, wherein the coupling circuitry comprises a first switch configured to couple the first signal line to a common electrical potential and a second switch configured to couple the second signal line to the common electrical potential.

7. The apparatus of claim 6, wherein the first switch and the second switch are arranged in series between the first signal line and the signal line and wherein a reference voltage defining the common electrical potential is applied to a signal path between the first switch and the second switch.

8. The apparatus of claim 1 wherein the frequency of a control signal controlling the coupling circuitry is higher than a highest frequency component of the measured biometric signal.

9. The apparatus of claim 1, wherein selective coupling is affected during a latter half of a time interval between consecutive sampling instants of an analog-to-digital converter.

10. The apparatus of claim 1, wherein a control signal controlling the coupling circuitry has the same frequency as a sampling frequency of the analog-to-digital converter but a different phase offset such that the coupling in the coupling circuitry is affected when the analog-to-digital converter is not taking a sample.

11. The apparatus of claim 1, wherein the apparatus further comprises a controller configured to receive a biometric signal from at least one of the electrodes, to analyze a signal quality of the received biometric signal, and to configure the coupling circuitry to couple the first signal line and the second signal line to the common electrical potential according to the analyzed signal quality of the received biometric signal.

12. The apparatus of claim 1, wherein the apparatus is a heart activity transmitter further comprising a communication circuitry configured to transmit the measured biometric signal in order to display the measured biometric signal through a user interface.

13. The apparatus of claim 1, wherein the signals sensed by the first electrode and coupled from the first electrode to the signal detection circuitry for measurement are heart activity signals.

14. The apparatus of claim 1, wherein the electrical potential difference is caused by movement of the first electrode with respect to a subject to which the first electrode is attached, and wherein said coupling circuitry is configured to reduce, by applying said selective coupling, the electrical potential difference caused by such movement.

15. An apparatus comprising:
a first signal line configured to couple signals from a first electrode to a signal detection circuitry for measurement of biometric signals sensed by the first electrode;
a second signal line configured to couple signals from a second electrode, different from the first electrode, to the signal detection circuitry for measurement of biometric signals sensed by the second electrode; and
coupling means for selectively coupling the first signal line and the second signal line to a common electrical potential so as to equalize electrical potential difference between the first electrode and the second electrode, wherein the selective coupling of the coupling means is synchronized with a clock signal controlling sampling instants of an analog-to-digital converter of the apparatus such that the selective coupling is performed between consecutive sampling instants of an analog-to-digital converter without performing selective coupling during sampling instants of the analog-to-digital converter.

16. The apparatus of claim 15, wherein the signals sensed by the first electrode and coupled from the first electrode to the signal detection circuitry for measurement are heart activity signals.

17. The apparatus of claim 15, wherein the electrical potential difference is caused by movement of the first electrode with respect to a subject to which the first electrode is attached, and wherein said coupling means are for reducing, by applying said selective coupling, the electrical potential difference caused by such movement.

* * * * *